United States Patent
Chen et al.

(10) Patent No.: US 11,959,101 B2
(45) Date of Patent: Apr. 16, 2024

(54) CELL ACTIVATION REACTOR AND CELL ACTIVATION METHOD

(71) Applicant: Industrial Technology Research Institute, Hsinchu (TW)

(72) Inventors: Ting-Hsuan Chen, Hsinchu County (TW); Kuo-Hsing Wen, Hsinchu County (TW); Ya-Hui Chiu, Yilan County (TW); Nien-Tzu Chou, Hsinchu (TW); Ching-Fang Lu, Hsinchu County (TW); Cheng-Tai Chen, Taoyuan (TW); Ting-Shuo Chen, Taoyuan (TW); Pei-Shin Jiang, Hsinchu (TW)

(73) Assignee: Industrial Technology Research Institute, Hsinchu (TW)

( * ) Notice: Subject to any disclaimer, the term of this patent is extended or adjusted under 35 U.S.C. 154(b) by 20 days.

(21) Appl. No.: 17/535,694

(22) Filed: Nov. 26, 2021

(65) Prior Publication Data
US 2022/0169985 A1 Jun. 2, 2022

Related U.S. Application Data

(60) Provisional application No. 63/118,749, filed on Nov. 27, 2020.

(51) Int. Cl.
*C12M 3/00* (2006.01)
*C12M 1/00* (2006.01)
(Continued)

(52) U.S. Cl.
CPC ........... *C12N 5/0636* (2013.01); *C12M 27/02* (2013.01); *C12M 27/20* (2013.01); *C12M 29/04* (2013.01); *C12M 35/06* (2013.01); *C12M 47/02* (2013.01)

(58) Field of Classification Search
CPC ............................. C12M 27/20; C12M 27/02
See application file for complete search history.

(56) References Cited

U.S. PATENT DOCUMENTS 6,395,516 B1 * 5/2002 Nienow ................ B01F 27/902
366/322
2008/0206734 A1 8/2008 Asgari
(Continued)

FOREIGN PATENT DOCUMENTS

| CN | 107988074 | 5/2018 |
| CN | 110431222 | 11/2019 |

(Continued)

OTHER PUBLICATIONS

"Search Report of Europe Counterpart Application", dated Jun. 14, 2022, p. 1-p. 10.
(Continued)

*Primary Examiner* — Nathan A Bowers
(74) *Attorney, Agent, or Firm* — JCIPRNET

(57) ABSTRACT

A cell activation reactor and a cell activation method are provided. The cell activation reactor includes a body, a rotating part, an upper cover, a microporous film, and multiple baffles. The body has an accommodating space, which is suitable for accommodating multiple cells and multiple magnetic beads. The rotating part is disposed in the accommodating space and includes multiple impellers. The microporous film is disposed in the accommodating space and covers multiple holes of the accommodating space. The baffles are disposed in the body. When the rotating part is driven to rotate, the interaction between the baffles and the impellers separates the cells and the magnetic beads.

10 Claims, 8 Drawing Sheets

(51) Int. Cl.
  *C12M 1/06* (2006.01)
  *C12M 1/42* (2006.01)
  *C12N 5/00* (2006.01)
  *C12N 5/0783* (2010.01)

(56) References Cited

U.S. PATENT DOCUMENTS

| | | |
|---|---|---|
| 2016/0257920 A1* | 9/2016 | Lin .................... C12M 33/14 |
| 2017/0349874 A1 | 12/2017 | Jaques et al. |
| 2019/0112567 A1 | 4/2019 | Scibek et al. |
| 2019/0269727 A1 | 9/2019 | Fachin et al. |
| 2020/0010826 A1 | 1/2020 | Liberti et al. |
| 2023/0025193 A1* | 1/2023 | Murugesan ........... B01F 35/513 |

FOREIGN PATENT DOCUMENTS

| | | |
|---|---|---|
| CN | 111971382 | 11/2020 |
| JP | S6174574 | 4/1986 |
| JP | S62190073 | 8/1987 |
| JP | 2009539408 | 11/2009 |
| JP | 2012531432 | 12/2012 |
| JP | 2015507024 | 3/2015 |
| JP | 2017035009 | 2/2017 |
| JP | 2019517248 | 6/2019 |
| JP | 2019528087 | 10/2019 |
| TW | I651411 | 2/2019 |
| WO | 2015005299 | 1/2015 |
| WO | 2019155031 | 8/2019 |
| WO | 2020161252 | 8/2020 |

OTHER PUBLICATIONS

"Office Action of Taiwan Counterpart Application", dated Aug. 22, 2022, p. 1-p. 3.

"Office Action of Japan Counterpart Application", dated Jan. 10, 2023, p. 1-p. 2.

\* cited by examiner

CELL ACTIVATION REACTOR AND CELL ACTIVATION METHOD

CROSS-REFERENCE TO RELATED APPLICATION

This application claims the priority benefit of U.S. Provisional Application No. 63/118,749, filed on Nov. 27, 2020. The entirety of the above-mentioned patent application is hereby incorporated by reference herein and made a part of this specification.

BACKGROUND

Technology Field

The disclosure relates to a cell activation reactor and cell activation method, and particularly to a cell activation reactor and cell activation method for promoting cell proliferation.

Description of Related Art

Cell culture is one of the important technologies in the field of biomedical science and technology. In the recent extensive research and optimized immunotherapy technology, T cells can be isolated from the biological samples of a patient, then the T cells can be cultured and expanded, the concentration of T cells can increase to a sufficient amount, and immunotherapy is further implemented to target and attack specific cancer cells exclusively and with low side effects.

In the cell culture process (especially for T cells), in addition to the general conditions (e.g., placed in a stable cell incubator, adding nutrient solution), the multi-dendrite magnetic beads can also be used to increase more contact with the surface area of the cells to stimulate cell activation, and then better quality and quantity amplification effect can be achieved. In this technical process, the cells tightly attached to the magnetic beads have to be separated from each other. After separation, the cells can be purified for the expansion culture cycle in the next stage. In the prior art, cell separation is generally performed by manual operation, and the operator needs to use a micropipette and a plastic container to transfer the liquids between the various machines. However, the manual operation is likely to cause problems, such as cell cross-contamination, biological waste infection concerns, longer operation time, and higher labor costs, thereby restricting cell culture research sites to only laboratory mode. When applied to immunotherapy, the manual operation is not popular in current cancer treatment methods due to its high price.

In summary, how to improve the experimental methods of manually separating cells, optimize the cell culture process, shorten the time for culturing cells, improve the quality of cell culture, and reduce costs have become increasingly important.

SUMMARY

The disclosure provides a cell activation reactor and a cell activation method, which are suitable for improving the experimental method of manually separating cells and capable of optimizing the cell culture process, reducing manual operation errors, and improving the reproducibility of the experiment.

The cell activation reactor of the disclosure includes a body, a rotating part, an upper cover, a microporous film, and multiple baffles. The body has an accommodating space formed by a closed end, a side portion, and an open end. The accommodating space is adapted for accommodating a cell culture medium containing multiple cells and multiple magnetic beads. The rotating part is disposed in the accommodating space and includes an axis and multiple impellers. The rotating part is adapted to be connected to a driver to be driven to rotate. The upper cover is detachably disposed above the body to cover the open end of the accommodating space. The upper cover has an opening, and the opening is disposed corresponding to a position of the rotating part, so that the axis of the rotating part penetrates through and is disposed in the opening, the end of the axis of the rotating part is exposed, and the driver is connected to the rotating part through the end. The microporous film is disposed at the closed end of the accommodating space, the closed end includes multiple holes therethrough, and the microporous film covers the holes. Multiple baffles are disposed on the side portion of the accommodating space. When the rotating part is driven to rotate, an interaction of the baffles and the impellers of the rotating part causes the cells to be separated from the magnetic beads.

The cell activation method of the disclosure uses the cell activation reactor to perform cell activation and includes steps as follows. A driver is started in a programmable manner and a rotating part is driven to rotate intermittently to disperse multiple cells and multiple magnetic beads, and the cells are removed and collected after static activation.

In summary, the cell activation reactor of the disclosure includes the body, the rotating part, the upper cover, the microporous film, and the baffles. Through the interaction of the baffles and the rotating part, the cells and the magnetic beads can be separated automatically. In addition, the microporous film at the closed end of the accommodating space of the body has multiple holes, and gas exchanges autonomously inside and outside the accommodating space through the holes. Therefore, the accommodating space of the body can be in an oxygen-rich environment. Accordingly, a static cell culture can be performed to improve the experimental method of manual cell separation, while optimizing the cell culture process, reducing manual operation errors, and improving the reproducibility of the experiment. In addition, the possibility of automation can be further increased, and the process is quantified to facilitate the development of cell production systems, thereby shortening the time for culturing cells, improving the quality of cell culture, and reducing the high labor costs in conventional technologies.

DESCRIPTION OF THE EMBODIMENTS

Figure 1:
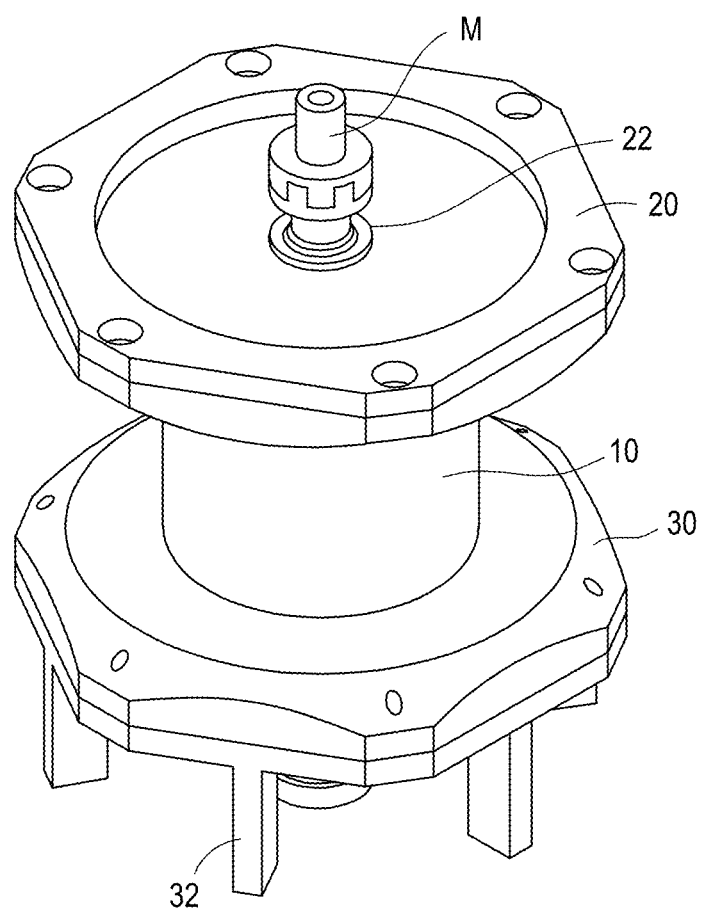
FIG. 1 is a schematic view of part of the structure of a cell activation reactor according to an embodiment of the disclosure.

Embodiments accompanied with drawings are described in detail below, but the embodiments are not intended to limit the scope of the disclosure. In addition, the drawings are for illustrative purposes only and are not drawn to scale. To facilitate understanding, the same elements may be described with the same reference numerals in the following description. Besides, terms "comprise", "include", "have", etc. used herein are all open-ended terms, namely meaning "including but not limited to" Furthermore, directional terminology mentioned in the specification, such as "upper" and "lower" etc., is used with reference to the orientation of the drawings being described. Therefore, the used directional terminology is not intended to limit the disclosure. In addition, the numbers and shapes mentioned in the specification are only used to specifically illustrate the disclosure to understand the content, but not to limit the disclosure.

In the specification, a range represented by "a numerical value to another numerical value" is a schematic representation for preventing listing all of the numerical values in the range in the specification. Therefore, the recitation of a specific numerical range covers any numerical value in the numerical range and a smaller numerical range defined by any numerical value in the numerical range, as is the case with the any numerical value and the smaller numerical range stated explicitly in the specification.

Figure 2:
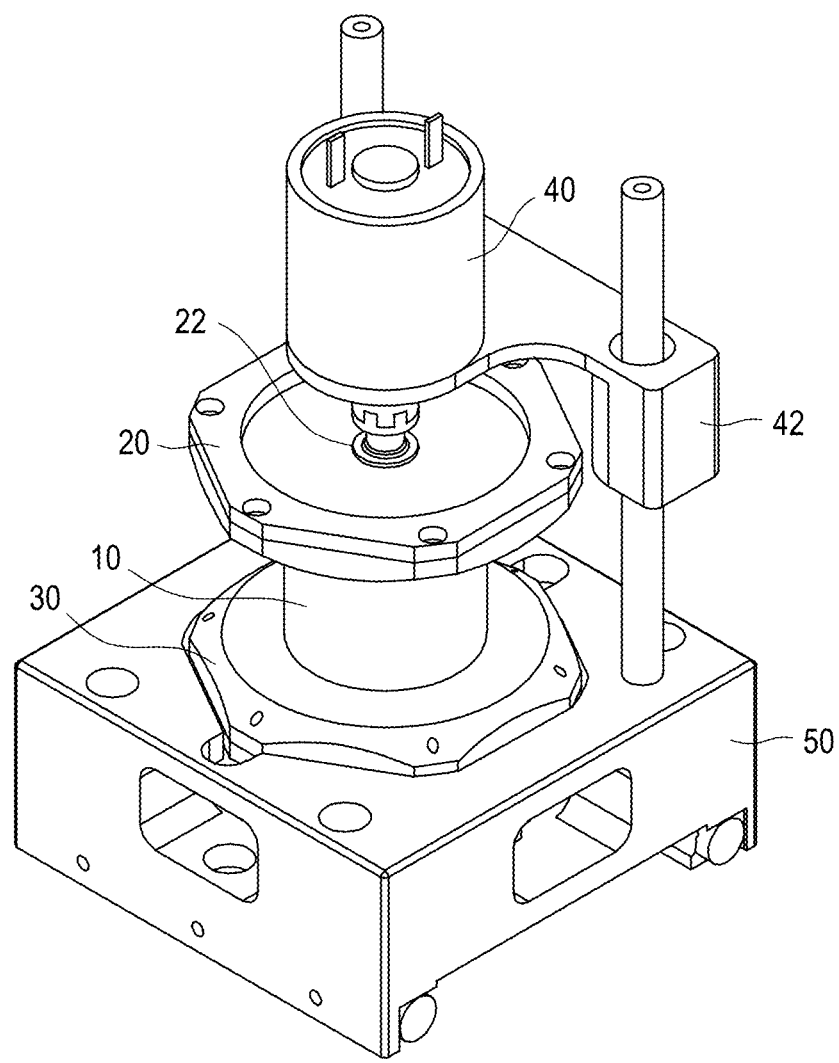
FIG. 2 is a schematic view of the structure of a cell activation reactor according to an embodiment of the disclosure.
Figure 3:
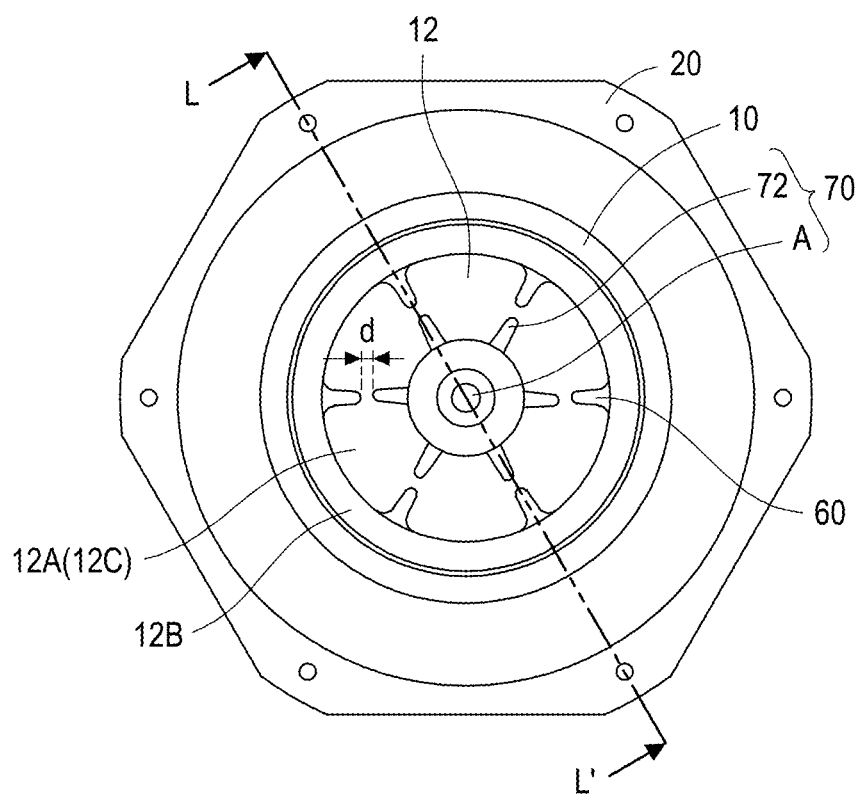
FIG. 3 is a schematic cross-sectional view of a junction between a body and an upper cover of a cell activation reactor according to an embodiment of the disclosure.
Figure 4:
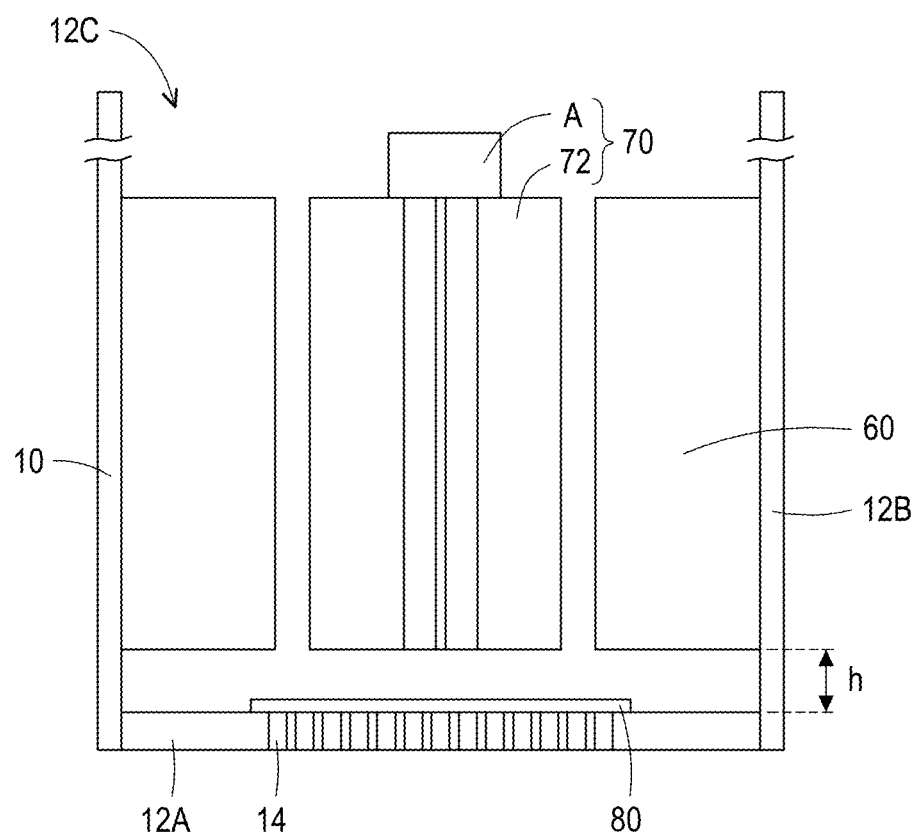
FIG. 4 is a schematic cross-sectional view taken along the section line L-L' in FIG. 3.
Figure 5:
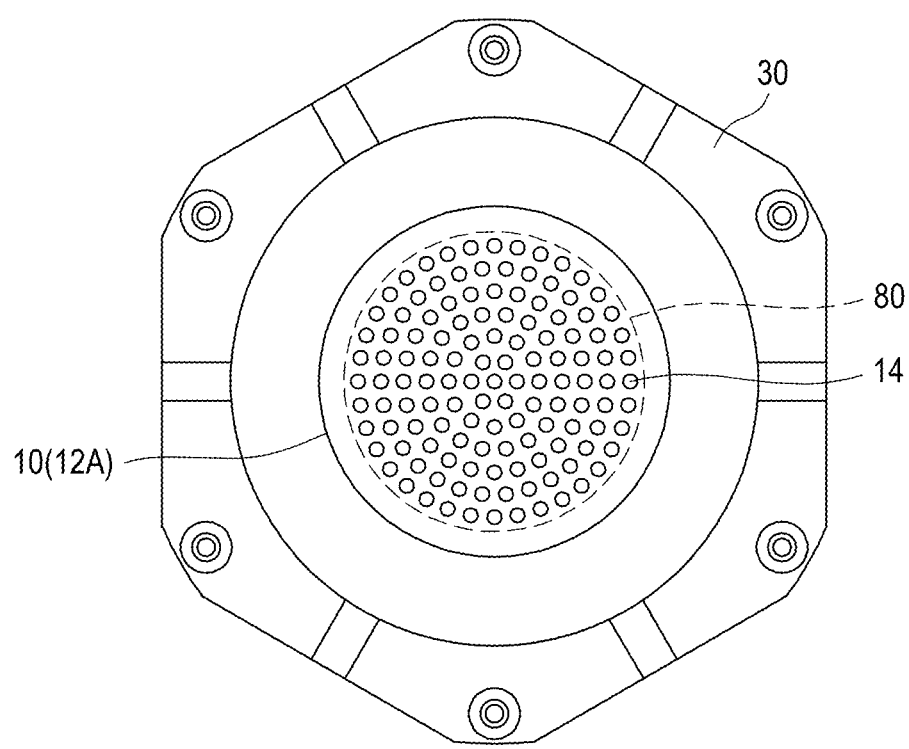
FIG. 5 is a schematic cross-sectional view of a junction between a body and a lower cover of a cell activation reactor according to an embodiment of the disclosure.

FIG. 1 is a schematic view of part of the structure of a cell activation reactor according to an embodiment of the disclosure. FIG. 2 is a schematic view of the structure of a cell activation reactor according to an embodiment of the disclosure. FIG. 3 is a schematic cross-sectional view of a junction between a body and an upper cover of a cell activation reactor according to an embodiment of the disclosure. FIG. 4 is a schematic cross-sectional view taken along the section line L-L' in FIG. 3. FIG. 5 is a schematic cross-sectional view of a junction between a body and a lower cover of a cell activation reactor according to an embodiment of the disclosure.

Referring to FIG. 1 first, the main components of the cell activation reactor include a body 10, an upper cover 20, and a lower cover 30. The upper cover 20 is detachably disposed above the body 10, and the lower cover 30 is disposed below the body 10. The materials of the body 10, the upper cover 20, and the lower cover 30 may include polycarbonate (PC). Referring to both FIG. 1 and FIG. 2, in addition to the main components shown in FIG. 1, the cell activation reactor may further include a driver 40, a bracket 42, and a base 50. The base 50 is disposed below the body 10, and the lower cover 30 may be embedded into the groove of the base 50. The driver 40 is disposed above the upper cover 20, and the bracket 42 is connected to the driver 40 and the base 50 to support the driver 40 to maintain a position above the upper cover 20. The driver 40 may include a motor, but the disclosure is not limited thereto.

Referring to FIG. 1, FIG. 2, and FIG. 3 altogether, the body 10 has an accommodating space 12, and the accommodating space 12 of the body 10 is formed by a closed end 12A, a side portion 12B, and an open end 12C. The accommodating space 12 is suitable for accommodating a cell culture medium containing multiple cells and multiple magnetic beads. In an embodiment, for example, the cavity volume of the accommodating space 12 is 20 mL. In other embodiments, the cavity volume of the accommodating space 12 may be 10-1000 mL. A rotating part 70 is disposed in the accommodating space 12 and includes an axis A and multiple impellers 72. The rotating part 70 is adapted to be connected to the driver 40 to be driven to rotate. In the embodiment, the upper cover 20 covers the open end 12C of the accommodating space 12, the upper cover 20 can define the position of the rotating part 70 through an opening 22 and can prevent the cell culture medium from leaking when the rotating part 70 is driven to rotate. Specifically, the upper cover 20 has the opening 22, the opening 22 is disposed corresponding to the position of the rotating part 70, so that the axis A of the rotating part 70 can protrude from the body 10 and penetrate through the opening 22 and expose the end M of the axis A of the rotating part 70. Accordingly, the driver 40 is connected to the rotating part 70 through the end M, so that the rotating part 70 can be driven by the driver 40 to rotate. The rotating part 70 has a rotation speed of 0-100 rpm, for example, and can be programmed to rotate. Multiple baffles 60 are disposed on the side portion 12B of the accommodating space 12, and the number of the impellers 72 may correspond to the number of the baffles 60, but the disclosure is not limited thereto. When the rotating part 70 is driven to rotate, since there is a relatively narrow gap between the baffles 60 and the impellers 72 of the rotating part 70, the baffles 60 interact with the impellers 72 of the rotating part 70 can separate the cells from the magnetic beads. In addition, the baffle 60 and the impeller 72 can increase the fluid shearing force. The detailed operation procedure for the separation of cells and magnetic beads may be described in detail below.

Referring to FIG. 1, FIG. 2, and FIG. 3 altogether, a minimum distance d between the impeller 72 and the baffle 60 is 1 mm, for example. In other embodiments, the minimum distance d between the impeller 72 and the baffle 60 may range from 1 to 8 mm. In the embodiment, the body 10 is cylindrical, for example. The axis of the body 10 and the axis A of the rotating part 70 can be overlapped, each impeller 72 extends from the axis A of the rotating part 70 toward the side portion 12B of the accommodating space 12, and the thickness thereof is gradually reduced. Each baffle 60 extends from the side portion 12B of the accommodating space 12 to the axis A of the rotating part 70, and the thickness thereof is gradually reduced to reduce cell rupture. The number of the baffles 60 is four or more, for example, and the number of the impellers 72 is four or more, for example. Although the numbers of the baffle 60 and the impeller 72 shown in FIG. 3 are 6 each, the disclosure is not limited thereto, and the number of the baffle 60 and the impeller 72 can be odd or even.

Referring to FIG. 1, FIG. 2, FIG. 3, and FIG. 4 altogether, for example, a distance h between the rotating part 70 and the closed end 12A of the accommodating space 12 is 0.05 mm to 1 mm, which can strengthen laminar flow and make fluid (i.e., cell culture medium) evenly stressed. In the embodiment, the cross-sectional shape of the impeller 72 is rectangular, for example.

Referring to FIG. 1, FIG. 2, FIG. 3, FIG. 4, and FIG. 5 altogether, note that in FIG. 4, only some of the elements are shown in response to the needs of the explanation, each element is only for illustration and mainly illustrates the configuration relationship between each element but does not represent the proportional relationship of the actual element size. In the embodiment, a microporous film 80 is disposed at the closed end 12A of the accommodating space 12 and includes a breathable and water-impermeable film material, such as a material including polytetrafluoroethylene (PTFE). In detail, the closed end 12A of the accommodating space 12 has multiple holes 14 penetrating vertically, and the microporous film 80 is disposed at the closed end 12A of the accommodating space 12 and covers the holes 14. Since the thickness of the microporous film 80 is very thin, the closed end 12A of the accommodating space 12 can include a supporting material, such as PC or nylon, so as to prevent the microporous film 80 from collapsing since the accommodating space 12 contains the cell culture medium. With the configuration of the microporous membrane 80 and the holes 14, the gas can be exchanged autonomously inside and outside the accommodating space 12, so that the cell culture medium can be maintained in an oxygen-rich environment. In one embodiment, the apertures of the holes 14 are 1.2 mm, for example and the area of the microporous film 80 is 490.87 $mm^2$, for example. In other embodiments, the apertures of the holes 14 may range from 0.6 to 1.5 mm, and the area of the microporous film 80 may range from 324 to 14400 $mm^2$.

In one embodiment, the lower cover 30 has multiple tripods 32 that can elevate the body 10 to expose the holes 14 so that when the cell activation reactor is disposed in a static manner, enough space is reserved for gas to flow in and out of the accommodating space 12 through the holes 14, and this provides the accommodating space 12 with an autonomous oxygen-rich environment and cells can be activated. In another embodiment, the cell activation reactor may further include the base 50, which is disposed under the body 10, and the lower cover 30 can be embedded in the groove of the base 50, so that the cell activation reactor can be more stable when disposed in a static manner, and meanwhile enough space is provided for gas to flow in and out.

Figure 6C:
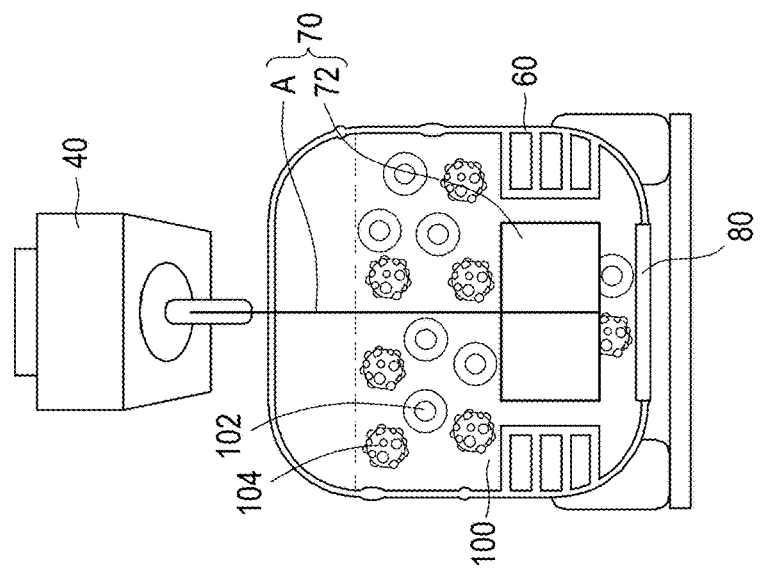
FIG. 6A to FIG. 6C are schematic cross-sectional views of an operation of a cell activation reactor according to an embodiment of the disclosure.
Figure 6B:
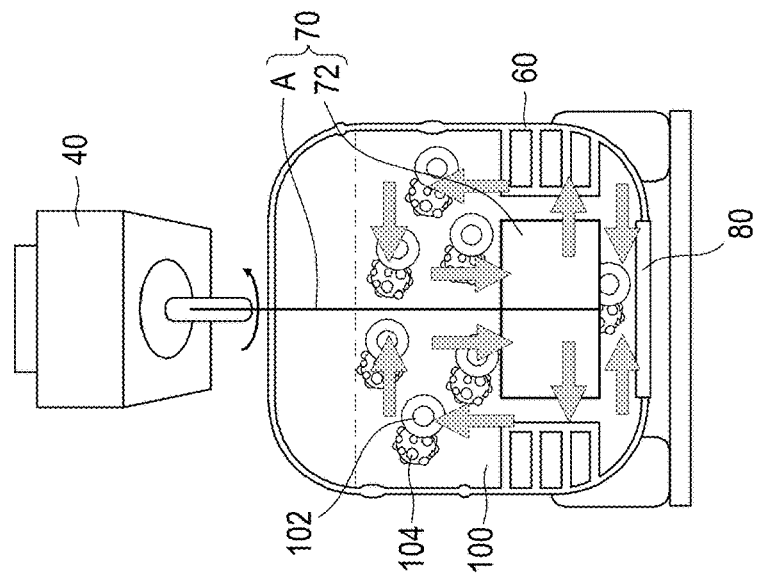
Figure 6A:
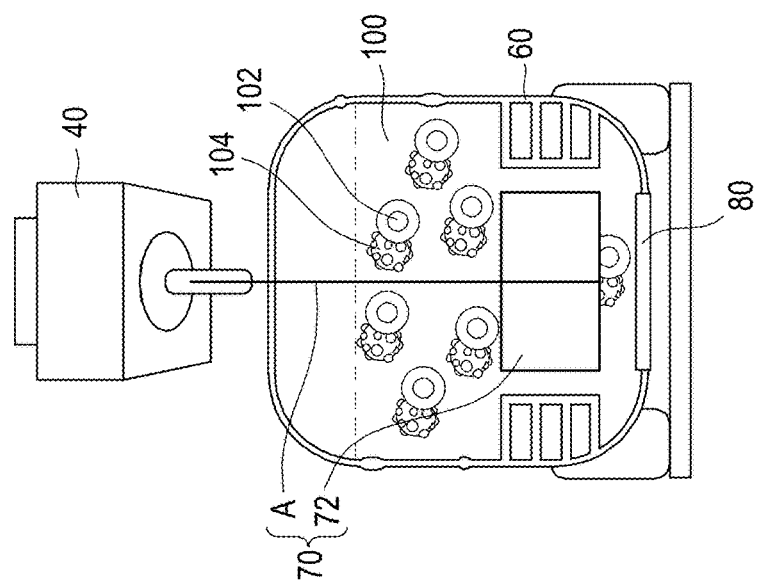

FIG. 6A to FIG. 6C are schematic cross-sectional views of an operation of a cell activation reactor according to an embodiment of the disclosure.

The disclosure also provides a cell activation method, which uses the cell activation reactor for cell activation, and the detailed operation process is shown in FIG. 6A to FIG. 6C. Referring to FIG. 6A, a cell culture medium 100 includes multiple cells 102 and multiple magnetic beads 104. Meanwhile, the cells 102 and the magnetic beads 104 are tightly combined. The initial quantity of the cells 102 in the cell culture medium 100 is $5\times10^5$ to $10\times10^5$, for example. Referring to FIG. 6B, when the rotating part 70 is connected to the driver 40 to be driven to rotate, the impellers 72 of the rotating part 70 interact to separate the cells 102 from the magnetic beads 104, the rotating part 70 is driven to rotate by the driver 40, and the baffles 60 and the impellers 72 can provide shearing force to separate the cells 102 and the magnetic beads 104, instead of manually operating a pipette to suck back and forth for cell separation in the prior art. In one embodiment, the driver 40 can be started programmatically, such as intermittently driving the rotating part 70 to rotate, so as to disperse the magnetic beads and cells.

Accordingly, referring to FIG. 6C, the cells 102 can be separated from the magnetic beads 104. Referring to FIG. 6A to FIG. 6C, the cross-sectional shapes of each impeller 72 and each baffle 60 are rectangular, for example. The height of each impeller 72 and each baffle 60 is the same, and the height of the liquid level of the cell culture medium 100 is greater than the height of each impeller 72, for example.

Hereinafter, experimental examples are used to illustrate the cell activation reactor and the cell activation method proposed in the disclosure in detail. However, the experimental examples are not intended to limit the disclosure.

EXPERIMENTAL EXAMPLE

To prove that the cell activation reactor and the cell activation method of the disclosure can effectively separate the cells from the magnetic beads, the experimental examples are specifically illustrated as follows.

Experimental Example 1

Figure 7:
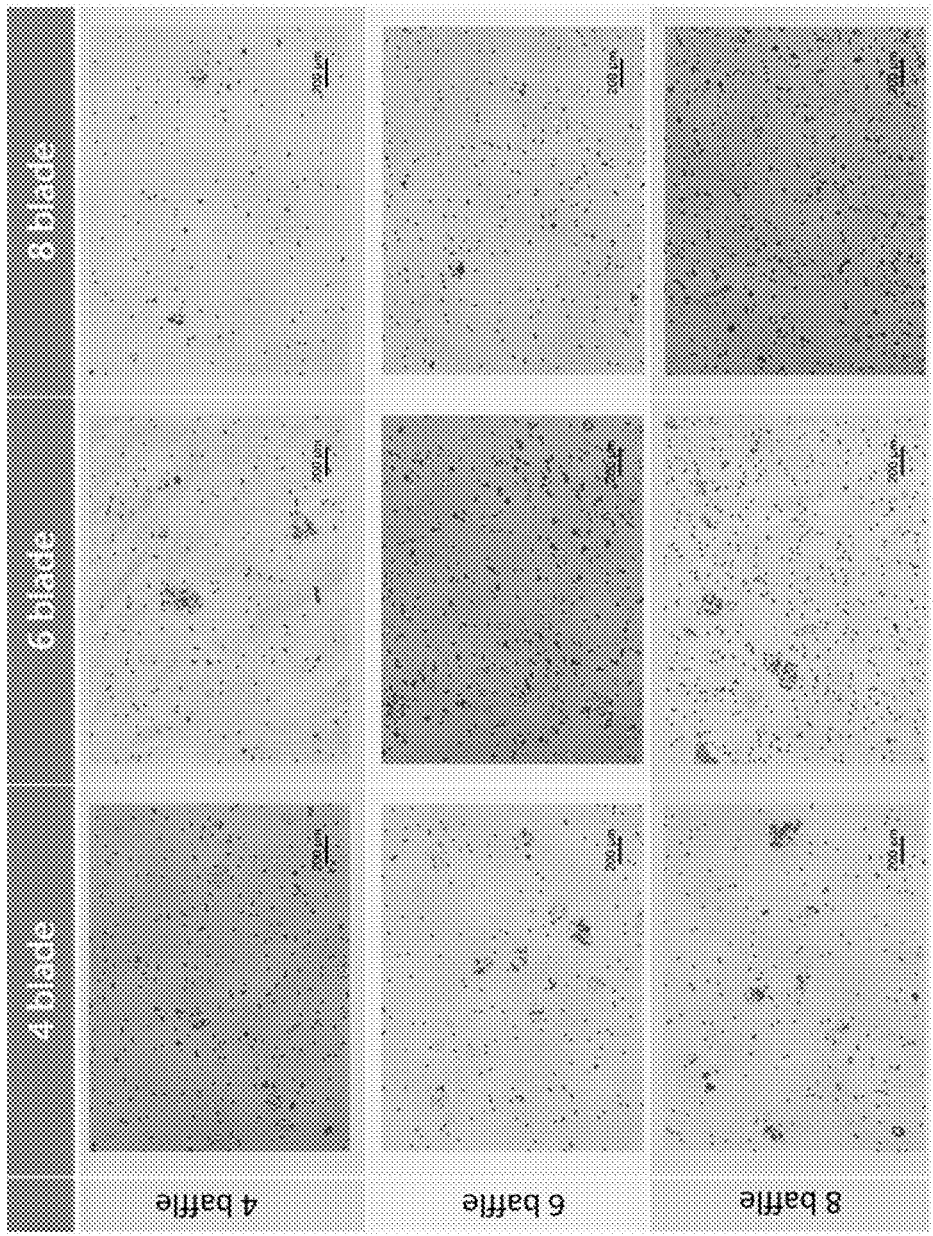
FIG. 7 is a microscopic view of a magnetic bead cell dispersion test with a cell activation reactor according to an embodiment of the disclosure.

A Magnetic Bead Cell Dispersion Test With Different Numbers of Baffles and Impellers FIG. 7 is a microscopic view of a magnetic bead cell dispersion test with a cell activation reactor according to an embodiment of the disclosure. Cell activation reactors with different numbers of baffles and impellers are configured to carry out the magnetic bead cell dispersion test. When the initial quantity of cells is $5\times10^5$, the rotation speed of the rotating part is at 100 rpm, rotates for 30 seconds, and stops for 30 seconds for 5 times. Then, a microscope is used to take a part of the field of view for shooting. Referring to FIG. 7, according to FIG. 7, when the number of baffles is 4 or more and the number of impellers is 4 or more, there is an effect of well-dispersed magnetic beads and cells well, and the magnetic beads and the cells can be entirely dispersed. In the embodiment, there is a favorable effect when 6 baffles and 6 impellers are configured.

Experimental Example 2

Comparison of Magnetic Bead Cell Dispersion Test

Figure 8:
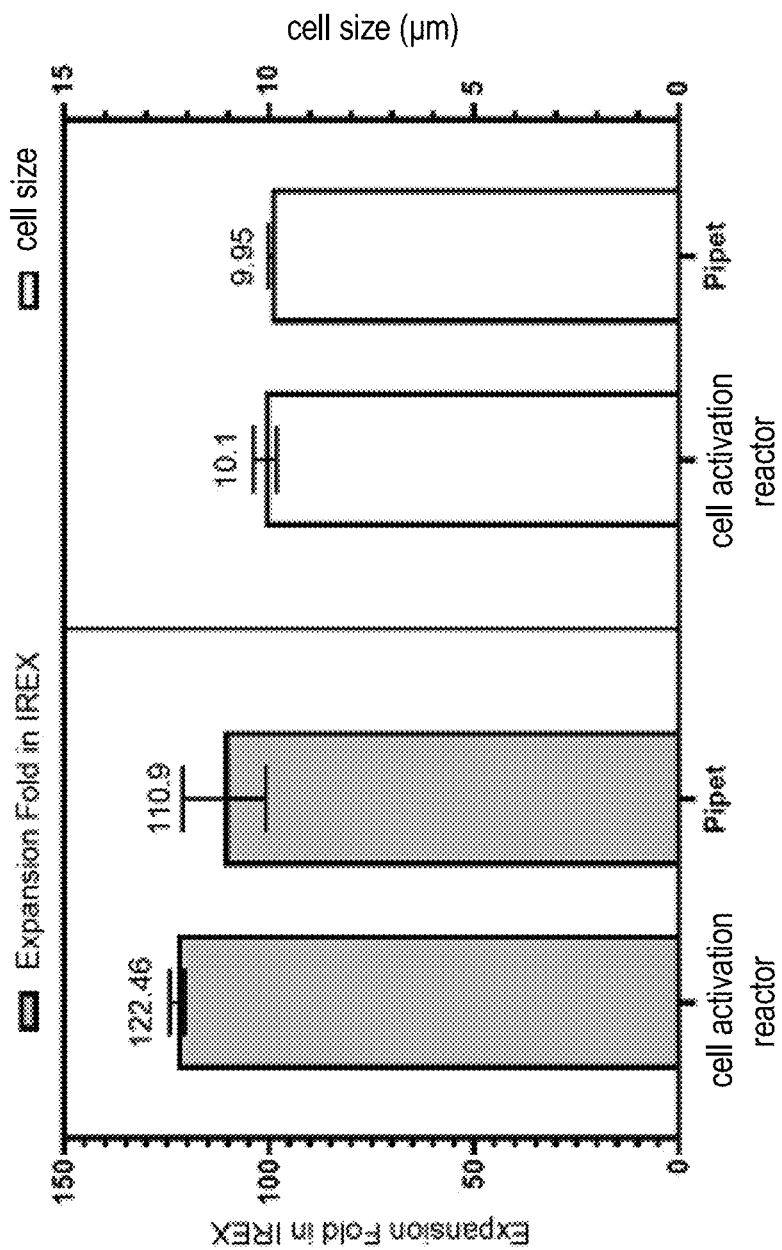
FIG. 8 illustrates cell viability and number measurement of a magnetic bead cell dispersion test with a cell activation reactor according to an embodiment of the disclosure.

FIG. 8 illustrates cell viability and number measurement of a magnetic bead cell dispersion test with a cell activation reactor according to an embodiment of the disclosure. In the experimental example, with the number of $5\times10^5$ T cells and iKNOBEAD magnetic beads, when the T cells and the magnetic beads are tightly combined, a manual pipette and the cell activation reactor of the disclosure are used to separate T cells and magnetic beads, respectively. After three days of the activation disposed in a static manner, the magnetic beads are removed and T cells are collected. Then, the T cells collected in the experimental group are removed from the cell activation reactor, and the T cells in the control group are cultured in a cell culture device for four days respectively, and then the cell viability and number are measured. Referring to FIG. 8, according to FIG. 8, compared to the manual pipette (corresponding to the pipet in FIG. 8), the cell activation reactor of the disclosure allows T cells and magnetic beads to have a good dispersion, which can reduce manual operation errors and has a high reproducibility.

In summary, the cell activation reactor of the disclosure includes the body, the rotating part, the upper cover, the microporous film, and the baffles. Through the interaction of the baffles and the rotating part, the cells and the magnetic beads can be separated automatically, and the fluid shear force can be strengthened and the viscous force can be cut off. The baffles can also accelerate the liquid convection. In addition, the microporous film at the closed end of the accommodating space of the body has multiple holes, and gas exchanges autonomously inside and outside the accommodating space through the holes. Therefore, the accommodating space of the body can be rich in oxygen to activate cells. Accordingly, static cell culture can be performed to improve the experimental method of manual cell separation, while optimizing the cell culture process, reducing manual operation errors, and improving the reproducibility of the experiment. In addition, the possibility of automation can be further increased, the process is quantified to facilitate the development of cell production systems, thereby shortening the time for culturing cells, improving the quality of cell culture, and reducing the high labor costs in conventional technologies.

What is claimed is:

1. A cell activation reactor, comprising:
   a body comprising an accommodating space formed by a closed end, a side portion, and an open end, wherein the accommodating space is adapted for accommodating a cell culture medium containing a plurality of cells and a plurality of magnetic beads;
   a rotating part disposed in the accommodating space, wherein the rotating part comprises an axis and a plurality of impellers, and the rotating part is adapted to be connected to a driver to be driven to rotate;
   an upper cover detachably disposed above the body to cover the open end of the accommodating space, wherein the upper cover comprises an opening, and the opening is disposed corresponding to a position of the rotating part, so that the axis of the rotating part penetrates through and is disposed in the opening, the end of the axis of the rotating part is exposed, and the driver is connected to the rotating part through the end;
   a microporous film disposed at the closed end of the accommodating space, wherein the closed end comprises a plurality of holes therethrough, and the microporous film covers the holes;
   a plurality of baffles disposed on the side portion of the accommodating space, wherein when the rotating part is driven to rotate, an interaction of the baffles and the impellers causes the cells to be separated from the magnetic beads; and
   a lower cover disposed below the body to elevate the body, wherein the body communicates with the lower cover through the microporous film,
   wherein the body is cylindrical, the axis of the body is overlapped with the axis of the rotating part, each impeller extends from the axis of the rotating part toward the side portion of the accommodating space, and a thickness there of is gradually reduced,
   wherein each baffle extends from the side portion of the accommodating space toward the axis of the rotating part, and a thickness thereof is reduced,
   wherein a height of each impeller and a height of each baffle are the same.

2. The cell activation reactor according to claim 1, wherein a minimum distance between the impeller and the baffle is 1-8 mm.

3. The cell activation reactor according to claim 1, wherein a number of the baffles is 4 or more, and a number of the impellers is 4 or more.

4. The cell activation reactor according to claim 1, wherein cross-sectional shapes of each impeller and each baffle are rectangular.

5. The cell activation reactor according to claim 1, wherein a distance between the rotating part and the closed end of the accommodating space ranges from 0.05 mm to 1 mm.

6. The cell activation reactor according to claim 1, wherein apertures of the holes range from 0.6 to 1.5 mm.

7. The cell activation reactor according to claim 1, wherein an area of the microporous film ranges from 324 to 14400 mm2.

8. The cell activation reactor according to claim 1, further comprising a base disposed below the body, wherein the lower cover is embedded in a groove of the base.

9. The cell activation reactor according to claim 1, wherein a height of a liquid level of the cell culture medium is greater than a height of each impeller.

10. A cell activation method using the cell activation reactor of claim 1 for cell activation, wherein the method comprises steps as follows:
   starting a driver in a programmable manner and enabling a rotating part to be driven to rotate intermittently to disperse a plurality of cells and a plurality of magnetic beads; and
   removing and collecting the cells after static activation.

* * * * *